(12) United States Patent
Krogh et al.

(10) Patent No.: US 9,149,737 B2
(45) Date of Patent: Oct. 6, 2015

(54) PURIFICATION OF MULTI-SPECIFIC RECEPTORS

(75) Inventors: Nicolas Otto Krogh, Virum (DK); Klaus Gregorius, Søborg (DK)

(73) Assignee: Mipsalus ApS, Virum (DK)

(*) Notice: Subject to any disclaimer, the term of this patent is extended or adjusted under 35 U.S.C. 154(b) by 0 days.

(21) Appl. No.: 13/496,006

(22) PCT Filed: Sep. 16, 2010

(86) PCT No.: PCT/EP2010/063614
§ 371 (c)(1),
(2), (4) Date: Mar. 14, 2012

(87) PCT Pub. No.: WO2011/033021
PCT Pub. Date: Mar. 24, 2011

(65) Prior Publication Data
US 2012/0171154 A1    Jul. 5, 2012

Related U.S. Application Data

(60) Provisional application No. 61/244,487, filed on Sep. 22, 2009.

(30) Foreign Application Priority Data

Sep. 16, 2009   (EP) .................................. 09170484

(51) Int. Cl.
*A61K 31/74* (2006.01)
*B01D 15/38* (2006.01)
*B01J 20/26* (2006.01)
*B01D 15/18* (2006.01)

(52) U.S. Cl.
CPC ............ *B01D 15/3804* (2013.01); *A61K 31/74* (2013.01); *B01J 20/26* (2013.01); *B01J 20/268* (2013.01); *B01D 15/1807* (2013.01)

(58) Field of Classification Search
None
See application file for complete search history.

(56) References Cited

U.S. PATENT DOCUMENTS 5,786,428 A * 7/1998 Arnold et al. ............... 525/333.3
5,994,110 A   11/1999 Mosbach 8,287,908 B2 * 10/2012 Kristensen et al. .......... 424/489
2004/0062745 A1   4/2004 Green
2006/0030027 A1   2/2006 Ellson

FOREIGN PATENT DOCUMENTS

| KR | 100 841 421 B1 | 6/2008 |
| WO | WO 02/070646 A2 | 9/2002 |
| WO | WO2007/095949 A2 | 8/2007 |
| WO | WO2010/057014 A2 | 5/2010 |

OTHER PUBLICATIONS

The International Preliminary Report on Patentability, PCT/EP2010/063614, issued Mar. 20, 2012.*
Levy, "Phenylketonuria: Old disease, new approach to treatment," PNAS, 1999, vol. 96, issue 5, pp. 1811-1813.*
Guerreiro, A.R., et al., "Selection of imprinted nanoparticles by affinity chromatography," *Biosensors and Bioelectronics*, Apr. 15, 2009, pp. 2740-2743, vol. 24(8); Elsevier B.V.
Piletsky, S.A., et al., "On the Role of Electrostatic Interactions in the Enantioselective Recognition of Phenylalanine in Molecularly Imprinted Polymers Incorporating β-Cyclodextrin," *Polymer Journal*, Oct. 15, 2005, pp. 793-796, vol. 37(10).

* cited by examiner

*Primary Examiner* — Galina Yakovleva
(74) *Attorney, Agent, or Firm* — Alston & Bird LLP

(57) ABSTRACT

Disclosed is a method for preparing a composition enriched for receptors (typically molecular impringet polymers, MIPs) that bind an agent, where said receptors each specifically bind at least two discrete sites on said agent, by subjecting a sample of receptors to a first step of affinity purification with the agent where one binding site on the agent is non-accessible for binding to the receptors and subsequently subjecting the purified receptors to at least one further step of affinity purification with the agent where a second binding site on the agent is non-accessible. Also disclosed is a method for treatment, amelioration or prophylaxis of a disease selected from the group consisting of phenylketonuria (PKU, Følling's disease), hyperphenylalaninemia (HPA), alcaptonuria (black urine disease), tyrosinemia, hypertyrosinemia, myasthenia gravis, histidinemia, urocanic aciduria, maple syrup urine disease (MSUD), isovaleric acidemia (isovaleryl-CoA dehydrogenase deficiency), homocystinuria, propionic acidemia, methylmalonic acidemia, and glutaric aciduria Type 1 (GA-I), galactosemia, comprising administering to the gastrointestinal tract of a patient in need thereof an effective amount of a composition of molecular imprinted polymers (MIPs), said composition being capable of binding a symptom provoking agent of said disease.

2 Claims, No Drawings

PURIFICATION OF MULTI-SPECIFIC RECEPTORS

CROSS-REFERENCE TO RELATED APPLICATIONS

This application is the U.S. National Stage of International Application PCT/EP2010/063614 filed Sep. 16, 2010, which designates the U.S and was published by the International Bureau in English on Mar. 24, 2011, and which claims the benefit of U.S. Provisional Application No. 61/244,487, filed Sep. 22, 2009 and European Patent Application No. 09170484.1, filed Sep. 16, 2009, all of which are hereby incorporated by reference in their entirety.

FIELD OF THE INVENTION

The present invention relates to the field of purification of complex receptors, i.e. receptors capable of binding several structures on a symptom provoking molecule such as an amino acid or a carbohydrate. The invention also relates to methods of treatment of a number of metabolic disorders, where biomolecules derived from an ordinary diet provoke disease symptoms in patients.

BACKGROUND OF THE INVENTION

Affinity chromatography is a method that takes advantage of the interaction between a molecule on the chromatography matrix and a binding partner for the molecule in order to select a subpopulation of binding partners from a larger pool of substances with varying affinity to the molecule or from a crude mixture, such as a fermentation stock.

Methods, such as affinity chromatography, that utilizes binding between molecules for the purpose of purification, analysis, diagnostics, etc are inherently limited by steric hindrance caused by the orientation of the molecule on the chromatoghraphy matrix and by the way it is coupled to a matrix (via a carrier molecule, a spacer, a linker etc). A consequence of this is that only a limited part of the molecule's total set of discrete binding sites is exposed to the receptor—those used for coupling to the matrix are not accessible to the binding partners which are brought into contact with the coated chromatography matrix.

In many cases, this does not present a problem, since only one particular binding characteristic of the binding partner is of interest.

When developing receptors, either so-called natural receptors such as antibodies, or synthetic receptors such as Molecular Imprinted Polymers (MIPs), selection/isolation of the best binding individual receptor entities—antibody molecules or MIP particles, either soluble or insoluble—is a means of improving the affinity, specificity, capacity etc of the resulting receptor based product—in relation to MIPs, cf. WO 2007/095949 where purification methods are disclosed which give rise to MIP compositions having improved binding affinity and capacity for a target molecule.

There is, however, a need to further improve the binding characteristics of compositions such as MIPs and polyclonal antibodies.

SUMMARY OF THE INVENTION

When preparing compositions of receptors for a target molecule, the affinity or avidity for binding to the target molecule depends on a number of factors. Relatively large receptor molecules such as polyclonal antibodies and MIPs bind to smaller targets at a number of different discrete sites on the targets and a purification method using the target molecule as capture agent on a chromatography matrix, where the target molecule is attached via one particular functional group will have the consequence that the purified product does not necessarily bind that functional group (because it is not accessible to binding after being coupled to the matrix). On the other hand, the very nature of such multi-site binding receptors is that the molecules obtained after a first round of purification will include receptors which at least partially bind the non-accessible site from the first round of purification. So if one devices further steps, which uses the same target molecule as capture agent, but bound via a different functionality, it should be possible to enrich further for those receptors which also exhibit a reasonably high affinity for the "hidden binding site" in the first purification step.

It will also be possible to enrich for receptors that bind a "characteristic" part of the intended target molecule—for each step of purification where a functionality is hidden via its binding to a matrix, the receptors which are dependent on the hidden functionality for their binding will be excluded during the purification procedure—so, if the target molecule includes non-characteristic functionalities which are shared with numerous other molecules (as is the case with amino acids that each have an N-terminus and C-terminus which are structurally identical from amino acid to amino acid), a multi-step purification procedure where each of the non-characteristic functionalities in turn are hidden should provide a composition of receptors which bind what is truly characteristic for the target molecule.

So, in a first aspect the present invention relates to a method for preparing a composition enriched for receptors that bind an agent, where said receptors each specifically bind at least two discrete sites on said agent, the method comprising
  a. providing a sample comprising said receptors,
  b. subjecting said sample to a first step of affinity chromatography, where said agent is used as affinity purification agent, and wherein said agent is immobilised to a solid or semi-solid phase via binding to one single of said at least two discrete sites,
  c. recovering receptors binding to the agent,
  d. subjecting receptors recovered in the previous step to at least one further step of affinity chromatography, where said agent is used as affinity purification agent, and wherein said agent is immobilised to a solid or semi-solid phase via binding to another of said at least two discrete sites, and recovering receptors binding to the agent,
wherein, in each said at least one further step of affinity chromatography, said another of said at least two discrete sites is different from any one of said at least two discrete sites, which has been used previously in steps b and d for immobilization of the agent to a solid or semi-solid phase.

In a second aspect, the present invention relates to a method for preparing a composition enriched for receptors that bind an agent, where said receptors each specifically bind at least two discrete sites on said agent, the method comprising preparing at least two compositions according to the method of the first aspect of the invention and subsequently combining said at least two compositions to obtain the composition enriched for receptors that bind the agent, wherein the same agent is used in steps b and d in the preparation of the at least two compositions, and wherein
  i. the combination of discrete sites in the agent, which are used for immobilization to the solid or semi-solid phase so as to prepare each of said at least two compositions, differ for at least two compositions, and/or ii. the sequential order in which discrete sites in the agent are used for immobilization to the solid or semi-solid phase so as to prepare each of said at least two compositions differ in the preparation of at least two of said at least two compositions.

In a third aspect, the present invention relates to a method for treatment, amelioration or prophylaxis of a disease selected from the group consisting of phenylketonuria (PKU, Følling's disease), hyperphenylalaninemia (HPA), alcaptonuria (black urine disease), tyrosinemia, hypertyrosinemia, myasthenia gravis, histidinemia, urocanic aciduria, maple syrup urine disease (MSUD), isovaleric acidemia (isovaleryl-CoA dehydrogenase deficiency), homocystinuria, propionic acidemia, methylmalonic acidemia, glutaric aciduria Type 1 (GA-1), and galactosemia, comprising administering to the gastrointestinal tract of a patient in need thereof an effective amount of a composition of molecular imprinted polymers (MIPs), said composition being capable of binding a symptom provoking agent of said disease. Related to this aspect is a composition of MIPs for use in such a method.

Finally, in fourth aspect the present invention relates to a method for the preparation of a pharmaceutical composition, the method comprising preparing a composition by use of the method of the first or second aspect of the invention and subsequently admixing the composition with a pharmaceutically acceptable carrier, diluent or vehicle.

DETAILED DISCLOSURE OF THE INVENTION

Definitions

The term "receptor" is herein used to designate a substance which exhibits affinity for and is capable of specifically binding an agent of interest, that is, a target. The term thus embraces what is normally termed biological receptor molecules but also other molecules which exert specific binding such as antibodies and molecular imprinted polymers. The quality of specific binding is in this context important, and effectively excludes substances which bind a number of unrelated targets; however cross-reactivity of a receptor for binding to seemingly unrelated molecules is not excluded, since this feature requires the existence of a common structural element in the two targets which are bound by the receptor. Typically, specific binding is characterized by a higher binding affinity to a target than to one or several irrelevant molecules which are used as negative controls in a binding assay.

A "molecular imprinted polymer" (MIP) is a polymer comprising cavities (or voids) that at least in part correspond to one or more template molecules that have been incorporated in a monomer matrix including cross-linking monomers prior to polymerization. The resulting polymer after polymerization includes a number of cavities which correspond in shape to the template molecule. Typically the MIP is sequestered into small particles, thereby facilitating removal of template and leaving partial cavities open for interaction with a target molecule which resembles or is identical to the template molecule. In the present specification and claims, the term MIP generally refers to any form of MIPs (soluble as well as insoluble), meaning that the terms "MIP" and "MIPs" are used interchangeably with the expressions MIP particle and MIP particles, respectively.

It will be understood that some MIPs purified or employed in the present invention are insoluble molecules/entities— this is e.g. the case for MIPs prepared according to the principles in WO 2007/095949. These MIPs are especially suitable as pharmaceuticals for use in the gastrointestinal tract since their insolubility limits or prevents their passage into the body (e.g. into circulation) from the gastrointestinal tract. In other words, when administered orally, the insoluble MIPs used in the present invention will substantially remain confined to the gastrointestinal tract until they are disposed off in the feces.

However, the MIPs purified according to the principles presented herein may also be soluble MIPs, which are useful in a number of different applications, where it is not of special interest to confine the MIPs to the gastrointestinal tract.

An "antibody" is a soluble biomolecule produced and secreted by B-lymphocytes in response to immunogical challenge. In the present context the term is mostly used to designate polyclonal antibodies, i.e. a mixture of antibodies produced by several clones of B-lymphocytes. The term may also designate antibodies or antibody fragments encoded by and bound to phage particles, which are used in phage display technology. Antibodies purified according to the invention may be of any antibody class, and can e.g. be of IgA, IgD, IgE, IgG and IgM class. Also non-human antibody species such as single chain antibodies (such as camel or llama antibodies) are within the scope of the term.

A "target molecule" is in the present context any molecule to which a receptor can specifically bind and is typically the molecule to which it is intended that the purified receptors should bind when ultimately using the receptors for a purpose. The term "target molecule" is in the present context used interchangeably with the term "agent", when discussing binding of a receptor with such an "agent", but it is to be noted that the "agent" used in the method of the invention does not necessarily have to be identical to the target molecule— rather, the agent is quite often a mimic or derivative of the target molecule which is useful for the purification steps discussed herein. The agent may e.g. constitute part of a larger molecule compared to the target molecule—for instance, if the intended target molecule is an amino acid, also the corresponding amino acid residue forming part of a protein or peptide may be useful as an agent in steps b and d. For example, the purification process may be set up to enrich for receptors that bind an amino acid residue, where one step in the purification employs a peptide where the amino acid is in the C-terminus, and where another step employs the amino acid in the N-terminus of a peptide—in such a case, the agent is the substance used in the purification steps, whereas the target molecule is considered to be the substances which are effectively bound by the enriched receptors.

Likewise, a "template molecule" is normally identical to a target molecule/agent, but may also be a mimic or derivative thereof (i.e. a molecule having at least in part an identical 3D structure and profile which matches that of the target molecule—a mimic may for instance be constituted by a fragment of the target molecule). The template serves as the "generator" of the voids in the MIP structure which subsequently are to be able to bind the target molecule.

It is also to be noted that the enriched receptor compositions (e.g. MIP compositions) may exert specific binding to other molecules than those used as templates or those used as agents in the method of the invention described herein. Therefore, such receptor compositions can be used in libraries that may be screened for binding to potential (and not necessarily related) target molecules. This can be compared to the technology of phage display, where phages expressing receptor molecules (e.g. antibody libraries) have been shown to bind molecules of completely different origin than the antigen originally used to bind the receptor molecules. For instance, on the $6^{th}$ International Meeting on Molecular Imprinting, Aug. 9-12, 2010, New Orleans, La., Dr. Ecevit Yilmaz (SE) presented published examples of MIPs showing cross reactivity to molecules very different in structure to the template molecule originally used in the MIPs synthesis process. Furthermore Dr. Yilmaz presented generic MIPs libraries that can be used to identify polymer compositions with affinity towards a specific target molecule. After such identification the selected polymer could be subjected to the affinity purification process described in this patent and thereby achieve MIPs with higher capacity than the raw unpurified MIPs.

"Affinity chromatography" denotes any method for purification of a receptor where specific binding between the receptor and a binding partner is utilised using an affinity purification agent bound to a solid support (such as a chromatographic matrix) which catches the substance. Typical examples known in the art are affinity purification using antibodies as capture agents coupled to chromatographic beads for purifying antigens that bind the antibody. It will be understood that the affinity purification methods applied according to the present invention are those which are capable of MIP particles having the characteristics discussed herein. Hence, a typical affinity purification method for insoluble MIPs could be expanded bed adsorption (EBA) known to a person skilled in the art.

A "solid or semi-solid phase" is in the present context any material which may be used to anchor a capture agent by means of covalent or non-covalent binding. Hence, any material (plastic polymers, sugars, metals, glass, silica, rubber etc) which is conventionally used in the preparation of chromatographic materials may serve as the solid phase. The solid phase material may contain suitable functional groups which allow coupling of the capture agent to the material in question. Such derivatized materials are known to the person skilled in the art of chromatographic purification of proteins and other macromolecules. Further, the solid phase may have any physical form which allows for capture of relatively large and insoluble particles such as MIPs (when comparing with single biomolecules such as proteins). Hence, the solid phase may be in the form of fibers (preferably hollow), a chromatography matrix (preferably a matrix suitable for EBA), beads (preferably those that may be separated by magnetic means) or any other suitable form, cf. below.

An oligonucleotide is a short sequence of nucleotides, typically having a length of at most 30 nucleotides, such as at the most 25, at most 20, at most 19, at most 18, at most 17, at most 16, at most 15, at most 14, at most 13, at most 12, at most 11, and at most nucleotide residues. Both RNA and DNA oligonucleotides are covered by the term.

An "oligonucleotide derivative" is intended to denote derivatised oligonucleotides, where the backbone is essentially the same as in an oligonucleotide, but where there are introduced chemical changes in the sugars of the ribose backbone, so the term includes within its scope such molecules as those which include LNA nucleotides in the sequence. However, the oligonucleotide derivatives may also be mimics of oligonucleotides such as PNA.

Embodiments of the First Aspect of the Invention

As mentioned above, the first aspect relates to a method for preparing a composition enriched for receptors that bind an agent, where said receptors each specifically bind at least two discrete sites on said agent, the method comprising
  a. providing a sample comprising said receptors,
  b. subjecting said sample to a first step of affinity chromatography, where said agent is used as affinity purification agent, and wherein said agent is immobilised to a solid or semi-solid phase via binding to one single of said at least two discrete sites,
  c. recovering receptors binding to the agent,
  d. subjecting receptors recovered in the previous step to at least one further step of affinity chromatography, where said agent is used as affinity purification agent, and wherein said agent is immobilised to a solid or semi-solid phase via binding to another of said at least two discrete sites, and recovering receptors binding to the agent, wherein, in each said at least one further step of affinity chromatography, said another of said at least two discrete sites is different from any one of said at least two discrete sites, which has been used previously in steps b and d for immobilization of the agent to a solid of semi-solid phase.

The principle thus allows for enrichment for those receptors in an initial composition, which bind to structures on the agent which encompasses both the accessible part of the agent in the first round of affinity chromatography and the accessible part of the agent in the second and any subsequent rounds of affinity chromatography.

As mentioned above, the agent can be part of a larger molecule—one practical example is the case where the target molecule is an amino acid such as phenylalanine (or other amino acid, cf. below) as well as short peptides that include the amino acid. In order to be able to enrich for receptors that bind the amino acid optimally, one may e.g. prepare a dipeptide, where the amino acid is present as the N-terminal amino acid residue and then couple the peptide to the solid or semi-solid phase in the first purification step. To enrich further, a dipeptide where the amino acid is now the C-terminal residue can be coupled to the solid or semi-solid phase in via its N-terminus in as subsequent purification step. The combined step will have enriched the composition for those receptors that bind parts of the amino acid which are not exclusively involved in peptide bonds or constitute the free N- or C-terminus.

The receptors are typically selected from the group consisting of molecular imprinted polymers (MIPs) and polyclonal antibodies, where it is desired to obtain an enriched mixture of these molecules, but the receptors may e.g. also be a population of phage particles that express antibody fragments on their surfaces. In essence, the technology then encompasses two rounds of panning against a capture agent, which has different orientations in the two rounds. Thus the present invention finds special use in situations where the receptor has a relatively large area of contact compared to the density of relevant surface areas on the target molecule.

The method of the first aspect is applicable in situations where the receptors are selected from soluble or insoluble MIPs and in one embodiment said receptors are insoluble MIPs. In another embodiment, said receptors are soluble MIPs.

In some embodiments said receptors are monospecific polyclonal antibodies. The term "monospecific" is intended to mean that the different antibodies constituting the polyclonal antibody all specifically bind the same agent.

The affinity chromatography may be performed by methods known to the skilled person. For example, the affinity chromatography may entail use of a fluidized bed system, such an expanded bed absorption system; this is particularly useful when the receptors are insoluble suspended molecules. However, the affinity chromatography may also be traditional column based chromatography (including HPLC and FPLC modes), which are particularly useful for soluble receptors.

In the above-described embodiments, the agent may be a chemical substance having the formula $H_3N^+$—CH(R)—$COO^-$, such as an amino acid, or the agent may be a peptide having at most 5 amino acid residues. The amino acid is typically selected from phenylalanine, tyrosine, histidine, leucine, methionine, isoleucine, tryptophan, threonine, valine and lysine. Also, the peptide is typically one, which includes within its sequence at least one amino acid selected from the group consisting of phenylalanine, tyrosine, histidine, leucine, methionine, isoleucine, tryptophan, threonine, valine and lysine. In particular embodiments, these amino acids appear as the N-terminal and/or C-terminal amino acid in the peptide.

In the embodiments where the agent is a peptide, it is typically a dipeptide, a tripeptide, a tetrapeptide or a pentapeptide.

In certain other embodiments of the first and second aspects of the invention described above, the agent is a carbohydrate, such as a branched or linear oligosaccharide having a maximum of 10 monosaccharide units. In certain embodiments, the carbohydrate is thus selected from a monosaccharide, a disaccharide, and a trisaccharide. Particularly interesting carbohydrates are D-galactose and lactose.

Also, the agent may be a fatty acid or a lipid; in the event the agent is a lipid, it is typically selected from the group consisting of cholesterol, a triglyceride, and a bile acid or a salt thereof.

Further, the agent can be an oligonucleotide or an oligonucleotide derivative, such as an oligonucleotide or oligonucleotide derivative selected from the group consisting of an RNA oligonucleotide, a DNA oligonucleotide, an LNA oligonucleotide, a PNA oligonucleotide, and a mixed oligonucleotide. In certain embodiments, the oligonucleotide or oligonucleotide deriveative is a mixed oligonucleotide, which comprises at least one ribo- or deoxoribunucleotide unit and at least one LNA or PNA nucleotide unit.

All the above embodiments may alternatively be utilised by employing agglutination instead of affinity chromatographic methods. In such embodiments of the first aspect of the invention, the isolation of the receptors is obtained by agglutination where the receptors form a "bridge" between several of the target agents.

Practical Considerations

The presently disclosed selection/isolation process may utilize a column loaded with a chromatography medium (the matrix) made of an insoluble material (typical examples are cross linked polysaccharides, polystyrene, glass etc.), where a molecule (the agent) is coupled via a (typically) covalent bond through a functional group to the matrix. The agent could as mentioned above be an amino acid, a peptide, a carbohydrate, cholesterol, a bile acid, a triglyceride, a fatty acid, etc. A solution or suspension of the receptor entities is applied to the chromatography medium (on a column or in an expanded bed system) and the receptor entities or receptor molecules with highest affinity to the exposed part of the agent will bind to the agent on the chromatography medium in a selection process and when eluted from the column this will result in provision of a subpopulation of receptor entities or molecules with higher affinity and higher capacity than the starting material.

If a second selection is performed on the selected receptor entities or molecules from the first selection, but now with the agent coupled to the chromatography medium with a different orientation than in the first selection, a new subpopulation of receptor entities or molecules that recognize both orientations of the agent will be the result. These double, or tandem, selected receptor entities or molecules will bind free, unbound, agent molecules with higher affinity, specificity, and capacity than the subpopulation of receptor entities or molecules from the first selection.

One example is purification of a population of MIPs that is polymerized with phenylalanine as target. The phenylalanine MIPs made by Piletsky and co-workers (Piletsky, S. A, Andersson, H, and Nicholls, I. A. Polymer Journal, 37 (2005) 793-796) has three potential target specific points of interaction: The phenyl ring, the amino group and the carboxylic group. In a subsequent selection or purification process using Expanded Bed Absorption (EBA) chromatography with phenylalanine as affinity agent, the phenylalanine molecule can be bound to the EBA medium either by the amine group or by the carboxylic group (or in principle also by the phenyl group if it was supplied with a reactive group). The MIPs may, however, as schematically illustrated in the paper by Piletsky, contain binding cavities that interacts with both the phenyl group plus the amino group, the phenyl groups plus the carboxylic group, the amino group plus the carboxylic group or the phenyl group plus both the amino and the carboxylic group simultaneously. If the phenylalanine MIPs are purified using expanded bed absorption, or another method that allows purification of insoluble particles by affinity to the target molecule, and the target molecule is immobilized on the chromatography matrix via e.g. the amino group of phenylalanine, then the MIPs that have the best binding to the phenyl ring and the carboxylic group simultaneously will be selected. This subpopulation of MIPs may contain another subpopulation of MIPs that predominantly has binding cavities that can interact also with the phenyl ring and the amino group. This sub-sub-population must have binding cavities that can interact with both the phenyl ring, the carboxylic group and the amino group simultaneously. The binding involving all 3 functional groups is expected to have a higher affinity and higher selectivity and will the give the MIP particles a higher binding capacity compared to MIP particles that predominantly have binding sites that only recognize two of the three potential points of interaction, i.e. discrete binding sites.

In a second example the phenylalanine MIP particles are grinded to a size where they become soluble. In that case the individual MIP particles will have fewer binding cavities compared to larger MIP particles and the chance that a given particle has predominantly one type of binding cavities, i.e. either binding cavities that can interact with all three functional groups on the phenylalanine molecule, or bindings cavities that interact with only two of the functional groups in phenylalanine etc. As in the first example, if a first purification, where the phenylalanine is immobilized to the chromatography matrix via the amino group, is followed by a second purification where the phenylalanine is immobilized to the chromatography matrix via the carboxylic group, the resulting sub-sub-population will predominantly have binding cavities that can interact with phenylalanine with both the phenyl ring, the carboxylic group and the amino group. In the case where the MIPs are soluble the chromatography does not necessarily have to be expanded bed absorption chromatography, but can be a conventional packed bed chromatography.

In a third example, an antibody is raised against an antigen with a complex set of epitopes and a high degree of stereo chemistry, e.g. a mono or disaccharide. When the saccharide agent is coupled to the chromatography matrix for affinity purification of the antibody, only a part of the total set of epitopes is exposed. The subpopulation of antibody molecules that are purified with the agent is in the said orientation may also contain another subpopulation of antibody molecules that recognizes a combination of epitope that are exposed in the said orientation plus a set epitopes that are exposed when the agent is differently orientated. This second subpopulation can be selected if the first subpopulation is applied to a second chromatography column with the saccharide agent coupled with another orientation. Such a second subpopulation may have higher affinity, higher selectivity and higher binding capacity than both the first subpopulation and the raw unpurified antibody.

Embodiments of the Second Aspect of the Invention

The method of the invention described in the first aspect results in enriched compositions of receptors which bind to a surface area on the target agent which includes binding cavities defined by all those functional groups used in each of the chromatographic steps.

However, it cannot be excluded that a fraction of the desired multi-site binding receptors are excluded in the first chromatographic step due to competition from receptors, which are subsequently excluded because they do not bind both the relevant discrete binding sites on the agent.

In order to fully exploit several binding cavities on a target, when preparing an enriched composition of receptors according to the principles of the present invention, one advantageous approach is therefore to run several affinity chromatographic procedures in parallel in each step, where the different procedures utilise binding of the agent to the chromatographic matrix via different discrete sites on the agent—after this, material enriched in the first step is subjected to the subsequent steps, still with different discrete binding sites utilised in the procedures in a step. Finally, the enriched compositions from each "arm" of consecutive purification steps are pooled. This ensures that the order of application of each chromatographic step does not result in an unintentional exclusion of receptors, which are actually capable of binding the desired large area on the agent.

One simple version of this approach entails use of binding of the agent via two different funcitonalities: the sample containing the receptor molecules are split in two portions, which are both subjected to the method of the first aspect of the invention, but the order of the chromatographic steps is reversed; finally the two resulting enriched fractions are pooled.

Formulated more generally, this second aspect of the invention entails a method for preparing a composition enriched for receptors that bind an agent, where said receptors each specifically bind at least two discrete sites on said agent, the method comprising preparing at least two compositions according to the method of the first aspect of the invention and any embodiment thereof and subsequently combining said at least two compositions to obtain the composition enriched for receptors that bind the agent, wherein the same agent is used in steps b and d in the preparation of the at least two compositions, and wherein
  i. the combination of discrete sites in the agent, which are used for immobilization to the solid or semi-solid phase so as to prepare each of said at least two compositions, differ for at least two compositions, and/or
  ii. the sequential order in which discrete sites in the agent are used for immobilization to the solid or semi-solid phase so as to prepare each of said at least two compositions differ in the preparation of at least two of said at least two compositions.

The preferred embodiments of this aspect are those wherein the same discrete sites in the agent are used for immobilization when preparing each of the at least two compositions, wherein the number of the at least two compositions equals the number of the at least two discrete sites, and wherein the sequential order in which the discrete sites are used for immobilization to the solid or semi-solid phase so as to prepare each of said at least two compositions is unique for each of the at least two compositions. Typically, the number of discrete sites is 2 or 3.

Embodiments of the Third Aspect of the Invention

The third aspect of the present invention relates to a method for treatment, amelioration or prophylaxis of a disease selected from the group consisting of phenylketonuria (PKU, Følling's disease), hyperphenylalaninemia (HPA), alcaptonuria (black urine disease), tyrosinemia, hypertyrosinemia, myasthenia gravis, histidinemia, urocanic aciduria, maple syrup urine disease (MSUD), isovaleric acidemia (isovaleryl-CoA dehydrogenase deficiency), homocystinuria, propionic acidemia, methylmalonic acidemia, and glutaric aciduria Type 1 (GA-1), galactosemia, comprising administering to the gastrointestinal tract of a patient in need thereof an effective amount of a composition of molecular imprinted polymers (MIPs), said composition being capable of binding a symptom provoking agent of said disease.

A number of inborn errors of metabolism are known where dysfunction in the metabolism of naturally occurring amino acids results in accumulation of pathological concentrations of metabolites or of the amino acids as such. For individuals suffering from such diseases, the daily food intake has to be managed in order to avoid the accumulation of these metabolites.

A typical example is the disease phenylketonuria. Individuals suffering from this disease are deficient in the enzyme phenylalanine hydroxylase (PAH). This enzyme is necessary to metabolize the amino acid phenylalanine to the amino acid tyrosine, meaning that phenylalanine accumulates in the patients and is converted into the metabolite phenylpyruvate. Left untreated, this condition can cause problems with brain development, leading to progressive mental retardation, and other neurological problems. Phenylketonuria is currently treated with a combination of a diet low in phenylalanine, often combined with treatment regimens which aim at lowering the blood level of phenylalanine so as to reach a safe and non-toxic concentration range. Lowering of phenylalanine levels to a safe range may be achieved by combining a low phenylalanine diet with medication.

The present invention offers an attractive alternative to the presently existing treatment regimens. By orally administering a composition of MIPs (typically insoluble MIPs, which due to their insolubility will with certainty not traverse gastrointestinal mucosa), which specifically bind phenylalanine and phenylalanine containing short peptides, entry into the bloodstream of toxic amounts of phenylalanine can be avoided or reduced. Also, the presence in the gastrointestinal tract of such MIPs will "drag" free phenylalanine over the gastrointestinal mucosa (by simply providing a larger capacity for bound phenylalanine in the gastrointestinal tract), thereby lowering the blood concentration thereof.

This particular principle is generally applicable for a number of other diseases where accumulation of free amino acids and/or their metabolites takes place due to deficiency in a metabolic enzyme. In principle, any composition of insoluble MIPs may be useful in this approach, but as demonstrated in WO 2007/095949, the typical composition of insoluble MIPs contains substantial amounts of MIPs which do not bind the desired target molecule—as a consequence, such compositions must be administered in very large amounts, whereas compositions prepared according to the methods disclosed in WO 2007/095949 or prepared according to the methods of the present invention will be far more effective since they are substantially devoid of non-binding MIPs. A particular attractive feature of the MIP compositions prepared according to the present invention (and those prepared according to WO 2007/095949) is the fact that such MIPs will not only bind the free amino acid in question but also short peptides which comprise the relevant amino acid in their amino acid sequence. So an important embodiment of this third aspect of the invention entails that the composition of MIPs is substantially free from MIPs which do not bind said symptom provoking agent.

Hence, treatment of the below-indicated inborn errors of metabolism by oral administration of MIPs that bind the corresponding targets (i.e. the disease provoking agent) is preferably done by using compositions of insoluble MIPs prepared according to the methods disclosed in 2007/095949 and more preferably insoluble MIPs prepared according to the 1$^{st}$ and 2$^{nd}$ aspects of the present invention, including all embodiments thereof.

In another embodiment of the third aspect of the invention, the disease is isovaleric acidemia (isovaleryl-CoA dehydrogenase deficiency) and the symptom provoking agent is L-leucine.

In another embodiment of the third aspect of the invention, the disease is homocystinuria and the symptom provoking agent is L-methionine.

In another embodiment of the third aspect of the invention, the disease is propionic acidemia, and the symptom provoking agent is L-isoleucine and/or L-valine and/or L-methionine and/or L-threonine.

| Target | Indication | Reference |
|---|---|---|
| L-Phenylalanine | Phenylketonuria (PKU) Hyperphenylalaninemia (HPA) | Chapter 77[1]: Hyperphenylalaninemia: Phenylalanine Hydroxylase Deficiency |
| L-Phenylalanine | Alcaptonuria | Chapter 92[2]: Alcaptonuria |
| L-Phenylalanine & L-Tyrosine | Tyrosinemia Hypertyrosinemia | Chapter 79[1]: Hypertyrosinemia |
| L-Histidine | Myasthenia Gravis | Chapter 91[1]: Disorders of β- and γ-Amino Acids in Free and Peptide-Linked Forms |
| L-Histidine | Histidinemia and Urocanic Aciduria | Chapter 80[1]: Disorders of Histidine Metabolism |
| L-Leucine | Maple Syrup Urine Disease (MSUD) | Chapter 87[1]: Maple Syrup Urine Disease (Branched-Chain Ketoaciduria) |
| L-Leucine | Isovaleric Acidemia (Isovaleryl-CoA Dehydrogenase Deficiency) | Chapter 93[2]: Branched Chain Organic Acidurias |
| L-Methionine | Homocystinuria | Chapter 88[1]: Disorders of Transsulfuration |
| L-isoleucine, L-valine, L-methionine & L-threonine | Propionic Acidemia, Methylmalonic Acidemia | Chapter 94[2]: Disorders of Propionate and Methylmalonate Metabolism |
| L-Tryptophane & L-Lysine | Glutaric Aciduria Type 1 (GA-1) | Chapter 95[2]: Organic Acidemias Due to Defects in Lysine Oxidation: 2-Ketoadipic Acidemia and Glutaric Acidemia |
| D-galactose | Galactosemia | Chapter 72[3]: Galactosemia |

Source: OMMBID—The Online Metabolic & Molecular Bases of Inherited Disease—
[1]Part 8: AMINO ACIDS,
[2]Part 9: ORGANIC ACIDS,
[3]Part 7: CARBOHYDRATES So, in one embodiment of the third aspect of the invention, the disease is phenylketonuria (PKU) and the symptom provoking agent is L-phenylalanine.

In another embodiment of the third aspect of the invention, the disease is hyperphenylalaninemia (HPA) and the symptom provoking agent is L-phenylalanine.

In another embodiment of the third aspect of the invention, the disease is alcaptonuria and the symptom provoking agent is L-phenylalanine.

In another embodiment of the third aspect of the invention, the disease is tyrosinemia and the symptom provoking agent is L-phenylalanine and/or L-tyrosine.

In another embodiment of the third aspect of the invention, the disease is hypertyrosinemia and the symptom provoking agent is L-phenylalanine and/or L-tyrosine.

In another embodiment of the third aspect of the invention, the disease is myasthenia gravis and the symptom provoking agent is L-histidine.

In another embodiment of the third aspect of the invention, the disease is histidinemia and the symptom provoking agent is L-histidine.

In another embodiment of the third aspect of the invention, the disease is urocanic aciduria and the symptom provoking agent is L-histidine.

In another embodiment of the third aspect of the invention, the disease is Maple syrup urine disease and the symptom provoking agent is L-leucine.

In another embodiment of the third aspect of the invention, the disease is methylmalonic acidemia, and the symptom provoking agent is L-isoleucine and/or L-valine and/or L-methionine and/or L-threonine.

In another embodiment of the third aspect of the invention, the disease is glutaric aciduria Type 1 (GA-1), and the symptom provoking agent is L-tryptophan and/or L-lysine.

Finally, in an embodiment of the third aspect of the invention, the disease is galactosemia and the symptom provoking agent is D-galactose and/or lactose.

The dosage regimen will depend of the MIP composition and its exact capacity for binding of the relevant disease provoking agent, the amount of symptom provoking agent to remove by means of the treatment and the constitution and age of the individual to be treated. The skilled artisan will be able to determine the relevant dosage parameters on a case by case bases.

With respect to formulation, the MIP particles prepared according to the present invention can be included in suspended or solubilised form in any convenient form, typically for oral administration. In certain embodiments, the MIP particles are simply suspended in water, optionally with addition of state-of-the art additives to improve taste (for oral compositions), colour, smell, consistency/texture, release, distribution, etc. It is also possible to integrate the MIP particles in foodstuffs and drinks which are prepared by simple admixture.

Embodiments of the Fourth Aspect of the Invention

The invention also entails preparation of a pharmaceutical composition, said method comprising preparing a composition according to the method of the first or second aspects of the invention, and subsequently admixing the composition with a pharmaceutically acceptable carrier, diluent or vehicle. The pharmaceutical composition is conveniently prepared so as to be suitable for oral administration, such as will be practical when the composition comprises insoluble MIP particles. However, if the composition comprises polyclonal antibodies or soluble MIP particles, the preparation will follow the standards for preparation of pharmaceuticals for parenteral administration.

The invention claimed is:

1. A method for treatment or amelioration of phenylketonuria (PKU, Følling's disease) comprising administering to the gastrointestinal tract of a patient in need thereof an effective amount of a composition of molecular imprinted polymers (MIPs), said composition being capable of binding L-phenylalanine.

2. A method for treatment or amelioration of phenylketonuria (PKU, Følling's disease) comprising administering to the gastrointestinal tract of a patient in need thereof an effective amount of a composition of molecular imprinted polymers (MIPs), said composition being capable of binding L-phenylalanine, wherein the composition of MIPs is prepared by i) obtaining a suspension of insoluble molecular imprinted polymers, which bind L-phenylalanine, and which have been prepared using L-phenylalanine as a template molecule, ii) subjecting the suspended molecular imprinted polymers to an affinity purification procedure, wherein L-phenylalanine is used as a capture agent, iii) recovering the molecular imprinted polymers that bind L-phenylalanine in the affinity purification procedure while substantially excluding L-phenylalanine and molecular imprinted polymers that do not bind L-phenylalanine from the recovered product, or prepared by a method comprising a. providing a sample comprising MIPs that bind at least two discrete sites on L-phenylalanine,
b. subjecting said sample to a first step of affinity chromatography, wherein L-phenylalanine is used as an affinity purification agent, and wherein L-phenylalanine is immobilized to a solid or semi-solid phase via binding to one single of said at least two discrete sites,
c. recovering MIPs binding to L-phenylalanine, and
d. subjecting MIPs recovered in the previous step to at least one further step of affinity chromatography, wherein L-phenylalanine is used as an affinity purification agent, and wherein L-phenylalanine is immobilized to a solid or semi-solid phase via binding to another of said at least two discrete sites, and recovering MIPs binding to L-phenylalanine wherein, said another of said at least two discrete sites is different from said one single of said at least two discrete sites.

* * * * *